United States Patent [19]

Satzinger et al.

[11] 4,022,818
[45] May 10, 1977

[54] 4r-AMINO-1t-PHENYL-1c-ETHOXY-CARBONYL-CYCLOHEXENES-(2) AND PROCESS FOR THEIR PREPARATION

[75] Inventors: Gerhard Satzinger, Denzlingen; Manfred Herrmann, Gundelfingen, both of Germany

[73] Assignee: Warner-Lambert Company, Morris Plains, N.J.

[22] Filed: June 10, 1975

[21] Appl. No.: 585,439

Related U.S. Application Data

[60] Division of Ser. No. 383,421, July 21, 1973, Pat. No. 3,905,978, which is a continuation-in-part of Ser. No. 226,509, Feb. 15, 1972, Pat. No. 3,957,851.

[30] Foreign Application Priority Data

Feb. 18, 1971   Germany .......................... 2107871

[52] U.S. Cl. .......................................... 260/471 A
[51] Int. Cl.$^2$ ..................................... C07C 101/38
[58] Field of Search ............................. 260/471 A

[56]    References Cited
UNITED STATES PATENTS 3,557,127   1/1971   Satzinger ................. 260/471 A X

*Primary Examiner*—Richard L. Raymond
*Attorney, Agent, or Firm*—Albert H. Graddis; Frank S. Chow; George M. Yahwak

[57] ABSTRACT

This invention relates to 4r-amino-1t-phenyl-1c-ethoxycarbonyl-cyclohexenes-(2) of formula I:

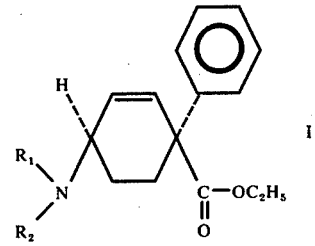

wherein $R_1$ and $R_2$ are the same or different and are hydrogen or alkyl having 1 to 4 carbon atoms, or one of the two groups is allyl, phenalkyl having 7 to 9 carbon atoms or α-methyl-β-hydroxyethyl; or $R_1$ and $R_2$ together form a morpholino group, piperazino group substituted at the 4- position by methyl, benzyl, phenyl, 3-chlorophenyl, 4-chlorophenyl, 2-phenethyl or benzoyl, or a piperidino group substituted at the 4- position by hydroxyl, phenyl, 2-methoxyphenyl, 4-methoxyphenyl, methyl or benzyl and medically acceptable addition compounds derived from inorganic and organic acids or lower alkyl halides. The compounds of the present invention are prepared by separation of 4-amino-1-phenyl-1-ethoxycarbonyl-cyclohexenes-(2), described in U.S. Pat. application Ser. No. 226,509, filed Feb. 15, 1972, now U.S. Pat. No. 3,957,851 into the two possible geometrical isomers. The instant compounds, the 4r-amino-1t-phenyl-1c-ethoxycarbonyl-cyclohexenes-(2) of formula I, exhibit marked analgesic and neuroleptic activities and are useful for the alleviation and reduction of pain.

3 Claims, No Drawings

4R-AMINO-1T-PHENYL-1C-ETHOXY-CARBONYL-CYCLOHEXENES-(2) AND PROCESS FOR THEIR PREPARATION

This is a division, of application Ser. No. 383,421 filed July 27, 1973, now U.S. Pat. No. 3,905,978, which in turn is a continuation-in-part of U.S. Ser. No. 226,509, filed Feb. 15, 1972, now U.S. Pat. No. 3,957,851.

BRIEF DESCRIPTION OF THE INVENTION

The compounds of formula I, in which the 1-phenyl substituent is trans to the 4-amino group, are obtained by fractional crystallization of compounds of formula II into its geometrical components, compounds of formula I and compounds of formula III. The 1-phenyl substituent is cis to the 4-amino group in compounds of formula III. The separation of the mixture of geometrical isomers into compounds of formulas I and III is also achieved by fractional crystallization of the salts and quaternary ammonium compounds corresponding to bases of formula II. The 4r-amino-1t-phenyl isomers of formula I are secured by thermolysis of the separated quaternary ammonium compounds of formula V. The synthesis of the amino esters depicted by formula II is described in our copending U.S. Pat. application Ser. No. 226,509, filed Feb. 15, 1972, now U.S. Pat. No. 3,957,851.

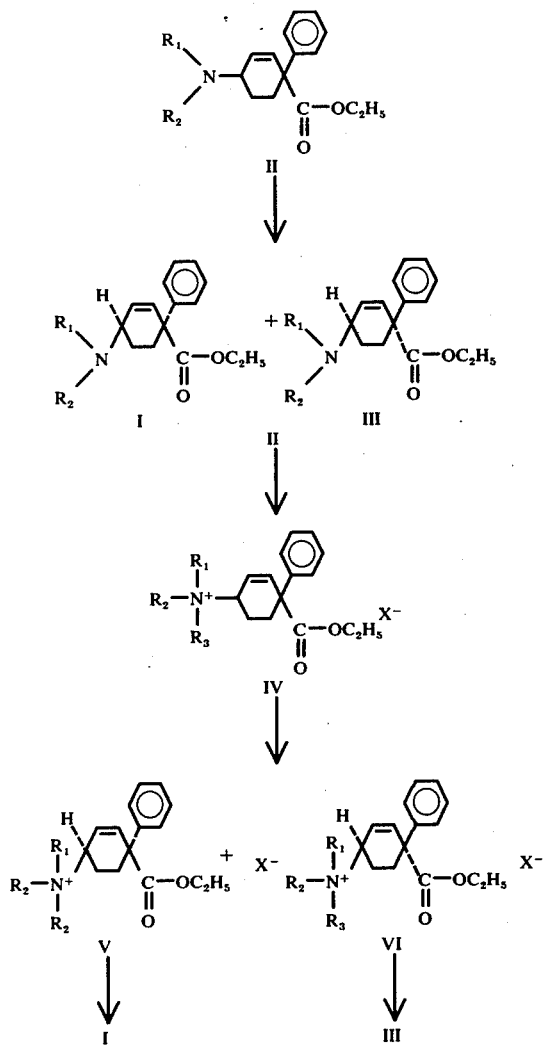

In formulas I to VI, $R_1$ and $R_2$ denote hydrogen, alkyl having 1 to 4 carbon atoms, allyl, phenalkyl having 7 to 9 carbon atoms or α-methyl-β-hydroxyethyl; $R_1$ and $R_2$ together for a morpholino group, a piperazino group substituted at the 4-position by methyl, benzyl, phenyl, 3-chlorophenyl, 4-chlorophenyl, 2-phenethyl or benzoyl, or a piperidino group substituted at the 4-position by hydroxyl, phenyl, 2-methoxyphenyl, 4-methoxyphenyl, methyl or benzyl; $R_3$ is alkyl having 1 to 4 carbon atoms and $X^-$ is an anion such as halide, methylsulfate or the like.

The aminoesters of formula I are converted to medically acceptable addition compounds derived from organic and inorganic acids or lower alkyl halides having 1 to 4 carbon atoms.

The aminoesters of formula I possess beneficial analgesic and neuroleptic properties as determined by the phenyl-p-quinone writhing test and the photocage, body temperature-reduction and aggression tests, respectively. The compounds of formula I are useful for the alleviation and reduction of pain.

DETAILED DESCRIPTION OF THE INVENTION

The synthesis and pharmacological properties of 4-amino-1-phenyl-1-ethoxycarbonyl-cyclohexenes-(2) of formula II are disclosed in our copending U.S. Pat. application Ser. No. 226,509, filed Feb. 15, 1972, now U.S. Pat. No. 3,957,851. The synthetic process described in the aforementioned application yields mixtures of amino esters of formula II, that is, amino esters in which the 1-phenyl group is cis or trans to the amino group attached to the 4-position of the cyclohexene ring. The amino esters so described exhibit analgesic and neuroleptic activity, a new and useful combination of pharmacological effects associated with a given chemical composition.

The present invention relates to 4r-amino-1t-phenyl-1c-ethoxycarbonyl-cyclohexenes-(2) of formula I wherein $R_1$ and $R_2$ are hydrogen, alkyl having 1 to 4 carbon atoms, allyl, phenalkyl having 7 to 9 carbon atoms or α-methyl-β-hydroxyethyl or $R_1$ and $R_2$ together form a morpholino group, a piperazino group substituted at the 4- position by methyl, benzyl, phenyl, 3-chlorophenyl, 4-chlorophenyl, 2-phenethyl or benzoyl or a piperidino group substituted at the 4- position by hydroxyl, phenyl, 2-methoxyphenyl, 4-methoxyphenyl, methyl or benzyl and medically acceptable addition compounds with inorganic and organic acids or lower alkyl halides of 1 to 4 carbon atoms.

The aminoesters depicted by stereostructure I are obtained by fractional crystallization of the aminoesters portrayed by structure II from a suitable solvent such as acetone, ethyl acetate, methanol, 2-propanol or benzene or mixtures thereof, followed by recrystallization of the stereo pure base of formula I from an aromatic hydrocarbon such as benzene or toluene. Salts, preferably hydrochlorides, of mixtures of isomeric aminoesters of formula II, prepared by treatment of said aminoesters with an inorganic acid, preferably hydrogen chloride, are also separated by fractional crystallization from the aforementioned solvent systems. Alternatively, quaternary ammonium compounds of formula IV, preferably methiodides, synthesized by treatment of the aminoesters of formula II with alkylating agents having 1 to 4 carbon atoms in the alkyl residue, preferably methyliodide are separated into the 1t-phenyl- and 1c-phenyl-quaternary ammonium compounds of formulas V and VI. The resolved ammonium compounds of formulas V and VI are converted into the corresponding ammonium acetates by exchange with an ion-exchange resin such as Amberlite IRA 400 (acetate form). The quaternary ammonium acetates of formulas V and VI wherein $X^-$ is acetate are thermally monodemethylated to the stereoisomeric amines of formula I and III. The thermal demethylation of the aforementioned acetates is performed at the boiling point of a solvent system composed of about 1 part by volume of acetonitrile to 3 parts by volume of toluene.

The aminoesters of formula I are transformed to salts, preferably hydrohalides, by dissolution of the base in a suitable solvent such as ether or 2-propanol followed by treatment of the solution with a hydrogen halide. For example, hydrochlorides of the amino esters of formula I are obtained when an ether or 2-propanol solution of compounds of formula I are treated with hydrogen chloride.

In the nomenclature of the compounds described in this invention, the lower case letters $r$, $c$, and $t$ mean reference radical, cis and trans, respectively, and refer to the relative geometry of the functional groups, the amino, ethoxycarbonyl and phenyl groups, with respect to the cyclohexene ring system. For example, in the name of the compound, 4$r$-amino-1$t$-phenyl-1$c$-ethoxycarbonyl-cyclohexene-(2), the letter $r$ preceding the term "amino" signifies that the amino group was arbitrarily chosen as the reference radical and in this case occupies the position above the average plane of the cyclohexene ring. The letter $c$ preceding the term "ethoxycarbonyl" denotes that the ethoxycarbonyl group is cis to the reference radical, that is, is located on the same side of the average plane of the cyclohexene ring as the amino group. The letter $t$ preceding the term "phenyl" means that the phenyl group is trans to the reference radical, that is, is situated on the opposite side of the average plane of the cyclohexene ring as the amino group. A solid line drawn from the cyclohexene ring to a substituent means that the group is situated above the average plane of the cyclohexene ring; a broken line means that the group is located below the plane.

The compounds of the present invention, 4$r$-amino-1$t$-phenyl-1$c$-ethoxycarbonyl-cyclohexenes-(2) of formula I, exhibit both analgesic and neuroleptic activity as shown by the data presented in the following chart:

| Substance (Hydrochloride) | Acute Toxicity LD 50 mg/kg (Mouse) | Analgesia ED 50 mg/kg Phenyl-p-Quinone Writhing Test | Reduction of Spontaneous Motility by % Photocage (Mouse) | Decrease in Body Temperature in ° C | Aggressive Mouse ED 50 mg/kg |
|---|---|---|---|---|---|
| Ethyl 1-methyl 4-phenyl-piperidin-4-carboxylate(Dolantin$^R$) | s.c. 154<br>i.g. 252 | s.c. 6.3<br>i.g. 28.5 | 15.0 mg/kg s.c.<br>30%<br>i.g. no effect | s.c. no effect<br>i.g. no effect | >15 mg/kg s.c.<br>i.g. no effect |
| (±)-3$r$-Dimethyl-amino-4$c$-phenyl 4$t$-ethoxycarbonyl-cyclohexene-(1) (Valoron$^R$) | s.c. 490<br>i.g. 437 | s.c. 15.9<br>i.g. 14.0 | s.c. no effect<br>i.g. no effect | s.c. no effect<br>i.g. no effect | s.c. no effect<br>i.g. no effect |
| 4$r$-Dimethyl-amino-1$t$-phenyl-1$c$-ethoxy carbonyl-cyclohexene-(2) (Example 1) | s.c. 155<br>i.g. 297 | s.c. 3.0<br>i.g. 13.6 | 5.0 mg/kg s.c.<br>38%<br>10.0 mg/kg s.c.<br>82% | 20 mg/kg s.c.<br>−1.4° | 4.0 mg/kg s.c. |
| 4$r$-(4'-Phenyl-piperidino-1')-1$t$-phenyl-1$c$-ethoxycarbonyl-cyclohexene-(2) (Example 3) | i.g. 800 | i.g. 10.0 | 25 mg/kg i.g.<br>91% | 50 mg/kg i.g.<br>−0.5° | 30 mg/kg i.g. |
| 4$r$-(4'-Phenyl-piperidino-1')-1$c$-phenyl-1$t$-ethoxycarbonyl-cyclohexene-(2) | i.g. 850 | i.g.<br>ca. 75.0 | 100 mg/kg i.g.<br>79% | i.g. no effect | i.g. no effect |
| 4$r$-(4'-Phenyl-piperazino-1')-1$t$-phenyl-1$c$-ethoxycarbonyl-cyclohexene-(2) (Example 5) | i.g. 1600 | i.g. 25.0 | 5.0 mg/kg s.c.<br>71%, 10.0 mg/kg i.g. 59%, 50 mg/kg i.g. 94% | 100 mg/kg i.g.<br>−2.6° | 25 mg/kg i.g. |
| 4$r$-Dimethyl-amino-1$c$-phenyl-1$t$-ethoxy-carbonyl-cyclohexene-(2) | s.c. 136<br>i.g. 490 | s.c. 14.6<br>i.g. 118.0 | 5.0 mg/kg s.c.<br>0%<br>20.0 mg/kg s.c.<br>25% | s.c. no effect | s.c. no effect |
| 4$r$-(Piperidino-1')-1$t$-phenyl-1$c$-ethoxy-carbonyl-cyclohexene-(2) (Example 2) | s.c. 150 | s.c. 5.3 | 10.0 mg/kg s.c.<br>93% | 25 mg/kg s.c.<br>−1.6° | 8.0 mg/kg s.c. |
| 4$r$-(Piperidino-1')-1$c$-phenyl- | s.c. 390 | s.c. >20.0 | 40.0 mg/kg s.c.<br>11% | 50 mg/kg s.c.<br>−0.1° | s.c. no effect |

-continued

| Substance (Hydrochloride) | Acute Toxicity LD 50 mg/kg (Mouse) | Analgesia ED 50 mg/kg Phenyl-p-Quinone Writhing Test | Reduction of Spontaneous Motility by % Photocage (Mouse) | Decrease in Body Temperature in °C | Aggressive Mouse ED 50 mg/kg |
|---|---|---|---|---|---|
| 1t-ethoxy-carbonyl-cyclohexene-(2) | | | | | |
| 4r-(4'-Phenyl-piperazino-1')-1c-phenyl-1t-ethoxycarbonyl-cyclohexene-(2) | i.g. ca. 1600 | i.g. >50.0 | 5.0 mg/kg s.c. no effect 10 mg/kg i.g. 34% | 200 mg/kg i.g. −1.7° | |
| 4r-[4'-(2-Methoxy-phenyl)piperazino-1']-1t-phenyl-1c-ethoxycarbonyl-cyclohexene-(2) (Example 4) | i.g. ca. 2000 | i.g. 50.0 | 50 mg/kg i.g. 86% | 200 mg/kg i.g. | no results so far |
| 4r-[4'-(2-Methoxy-phenyl)piperazino-1']-1c-phenyl-1t-ethoxycarbonyl-cyclohexene-(2) | i.g.>1600 | i.g.>150.00 | 50 mg/kg.i.g. 17% | — | — |

The lethal dose (LD)-50 values were determined in mice by acute toxicity measurements. Analgesic activity was ascertained in mice utilizing the phenyl-*p*-quinone writhing test and the results are presented in effective dose (ED)-50 values. Neuroleptic activity was determined in three pharmacological tests; the photocage, the body temperature reduction and aggressive mouse tests. The results are given in the dose required to obtain the indicated effect for the photocage and body temperature reduction tests and in effective dose - 50 values for the aggressive mouse test. The test compounds were administered subcutaneously (s.c.) and intragastrically (i.g.).

The methodology employed for the determination of the acute toxicity values and analgesic and neuroleptic activity (by the photocage and body temperature reduction tests) is described in German Patent Application No. P 21 07 871.7-42 and is presented in Examples 6, 8 and 9, respectively, of this application. In addition to the photocage and body temperature reduction tests, the aggressive mouse test was utilized to further define the neuroleptic (major tranquilization) activity of the compounds included in the chart.

When male mice are isolated in cages, some of the animals develop the habit of furiously defending their territory against intruders of the same sex. Experiments which influence this aggression can be used for the testing of inhibitory acting psychotropic drugs. The aggressive behavior can be influenced by neuroleptics (major tranquilizers) and tranquilizers (minor tranquilizers). Neuroleptics suppress the aggressive behavior at doses which do not influence motor activity and "minor tranquilizers" are effective only at high doses, which often produce ataxia.

Test animals were male mice (NMRI) which were isolated in Makrolon cages for at least 5 weeks. After this period a preliminary test was made to show which animals reacted aggressively within one minute to an animal of the same sex brought into the cage. Animals which had not become aggressive or which showed no reaction within one minute were not used in the main test performed two days after the preliminary test. On the test day the mice, fasted and isolated for 16 hours, were administered the test substance and the aggressive behavior towards a partner of the same sex was studied after 30 minutes. As in the preliminary test, the criterion was aggressive behavior within one minute. Each test group consisted of 6 animals. Animals which did not show aggressive behavior within one minute were regarded as protected. The Ed-50 values were determined. The 4r-amino-1t-phenyl-1c-ethoxycarbonyl-cyclohexenes-(2) of formula I, the compounds of this invention, are effective analgesics when administered orally to mammals such as mice and rats at a dose level of about 5 to 75 mg/kg of body weight, more particularly at a dosage of about 10 to 50 mg/kg of body weight. The dosage regimen may be different in other mammalian species depending upon factors well-known to those skilled in the medical arts.

The compounds of formula I can be formulated into various dosage forms for oral, parenteral or rectal administration. Included in these dosage forms are tablets, capsules, suspensions, emulsions, syrups, suppositories and other liquid and solid compositions known to those skilled in the pharmaceutical arts. Among the inert excipients formulated with the analgesic-neuroleptic compounds of formula I are gelatin, lactose, starches, water, oils, gums, polyalkylene glycols, petroleum jelly and other compatible adjuvants routinely used for the preparation of medicaments. In addition, preservatives, stabilizers, buffers, wetting agents, etc. may be included in the formulations. The aforementioned dosage forms are prepared by conventional methods and techniques.

The compounds of formula I, in which the 4-amino and 1-phenyl substituents are located on opposite sides of the average plane of the cyclohexene ring, exhibit both analgesic and neuroleptic activity, a desirable and beneficial combination of biological effects for the treatment of conditions involving acute pain. At present, combinations of analgesics and neuroleptics such as phenothiazines are used to both alleviate pain and calm the subject, that is, to achieve the same overall beneficial effect as obtained with the compounds of this invention, compounds of formula I. The combination of analgesic and neuroleptic activities associated with a single chemical entity is not only unknown in the prior art but is also an unexpected result. An equally unexpected result is the experimental observation that the corresponding geometric isomers of compounds of formula I, the 4r-amino-1c-phenyl-1t-ethoxycarbonyl-cyclohexenes-(2) of formula III, in which the 4-amino and 1-phenyl substituents are cis, are not only less potent analgesics than compounds of formula I but are essentially devoid of neuroleptic activity.

Several of the compounds of formula I, particularly 4r-dimethylamino-1t-phenyl-1c-ethoxycarbonyl-cyclohexene-(2), are more potent analgesics than (±)-3r-dimethylamino-4c-phenyl-4t-ethoxycarbonyl-cyclohexene-(1) (Valoron $^R$), a positional isomer of the former and Dolantin $^R$, the dominant analgesic for acute pain. Valoron $^R$ and Dolantin $^R$ possess no significant neuroleptic activity.

The following examples serve to illustrate the embodiment of the invention and are not to be construed as limiting the scope of the invention.

EXAMPLE 1

4r-Dimethylamino-1t-phenyl-1c-ethoxycarbonyl-cyclohexene-(2)

273 g of 4-Dimethylamino-1-phenyl-1-ethoxycarbonyl-cyclohexene-(2) (isomeric ratio 1tphenyl/1= 3/7 according to GC-analysis) dissolved in 3 L of benzene, are mixed with 142 g of methyl iodide and stored at 20° C for 24 hours. The crystalline mixture of the methiodides (yield 400 g) is collected and fractionally recrystallized from acetone. 120 g of pure 4r-dimethylamino-1t-phenyl-1c-ethoxycarbonyl-cyclohexene-(2) · methiodide, m.p. 175° C, are obtained as the more soluble component. The substance is dissolved in 2.4 L of methanol; the solution is run through a column filled with amberlite IRA 400 in the acetate form. The residue of the methanolic eluant is freed from traces of water by azeotropic destillation with toluene and is then taken up in a mixture of 2.25 L of acetonitrile and 6.7 L of toluene. The solution is heated under reflux for 16 hours. After removal of the solvent, the residue is dissolved in fresh toluene, washed with a small volume of $KHCO_3$-solution and then with water, and freed from the toluene under reduced pressure. The basic residue is precipitated from ether as hydrochloride by means of HCl-gas. Yield 41.0 g (46% of theory) of the 1t-phenyl compound as hydrochloride, m.p. 173°–175° C; GC-purity 99%.

$C_{17}H_{24}ClNO_2$ (309.85) Calc.: C - 65.89; H - 7.81; Cl - 11.45; N - 4.52; Found: C - 65.98; H - 7.86; Cl - 11.74; N - 4.80.

EXAMPLE 2

4r-(Piperidino-1')-1t-phenyl-1c-ethoxycarbonyl-cyclohexene-(2)

31.3 of 4-Piperidino-1-phenyl-1-ethoxycarbonyl-cyclohexene-(2) (isomeric ratio 1t-phenyl/1c phenyl = 6.5/3.5 according to GC analysis) are dissolved in 500 cc of ether and transformed into the crystalline mixture of the isomeric hydrochlorides (yield 34.0 g) by means of HCl-gas dissolved in ethyl acetate. The less soluble hydrochloride of the 1t-phenyl-compound is obtained in 96% purity by fractional crystallization from isopropanol/methanol (9:1) and in 99% purity (GC-determination) by subsequent recrystallization from isopropanol free from methanol. Yield 9.1 g, m.p. 221°–223° C.

$C_{20}H_{28}ClNO_2$ (349.9) Calc.: C - 68.65; H - 8.06; Cl - 10.13; N - 4.00; Found: C - 68.76; H - 8.04; Cl - 10.27; N - 4.18.

EXAMPLE 3

4r-(4'-Phenylpiperidino-1')-1t-phenyl-1c-ethoxycarbonyl-cyclohexene-(2)

39 g of 4-(4'-Phenylpiperidino-1')-1-phenyl-1-ethoxycarbonyl-cyclohexene-(2) (isomeric rate according to TLC 1t-phenyl/1c-phenyl = 7.5/2.5) are transformed into the hydrochloride as in Example 2. The less soluble 1t-phenyl-isomer is obtained TLC pure by fractional crystallization from isopropanol and subsequent recrystallization from toluene. Yield 12.0 g, m.p. 238°–240° C (m.p. of the pure trans-isomer 203°–205° C, mix-m.p. 215°–220° C)

$C_{26}H_{32}ClNO_2$ (426.01) Calc.: C - 73.30; H - 7.57; Cl - 8.32; N - 6.13; Found: C - 73.62; H - 7.52; Cl - 8.06; N - 3.48.

EXAMPLE 4

4r-[4'-(2-Methoxyphenyl)piperazino-1']-1t-phenyl-1c-ethoxycarbonyl-cyclohexene-(2)

42.1 g of 4-[4'-(2-Methoxyphenyl)piperazino-1']-1-phenyl-1-ethoxycarbonyl-cyclohexene-(2) (isomeric ratio according to TLC 1t-phenyl/1c-phenyl = 7/3), dissolved in ether, are transformed into the hydrochloride as in Example 2. The isomers are separated by fractional crystallization from benzene. The sparingly soluble 1t-phenyl-isomer is obtained in pure form by subsequent recrystallization from toluene. Yield 12.3 g, m.p. 182°–183° C.

$C_{26}H_{33}ClN_2O_3$ (457.03) Calc.: C - 68.33; H - 7.28; Cl - 7.76; N - 6.13; Found: C - 68.21; H - 7.40; Cl - 7.80; N - 6.28.

EXAMPLE 5

14r-(4'-Phenylpiperazino-1')-1t-phenyl-1c-ethoxycarbonyl-cyclohexene-(2)

39 g of 4-(4'-Phenylpiperazino-1')-1-phenyl-1-ethoxycarbonyl-cyclohexene-(2) (isomerism according to TLC 1t-phenyl/1c-phenyl = 3:2) are fractionally crystallized from ethanol (96%). 20 g of 1t-phenyl-isomer, obtained in 80% purity, are obtained in pure form by recrystallization from methanol or n-hexane. Yield 15 g, m.p. 95°–96° C. The hydrochloride is precipitated from isopropanol by means of HCl-gas. M.P. 207°–208° C.

$C_{25}H_{31}ClN_2O_2$ (426.9) Calc.: C - 70.33; H - 7.32; Cl - 8.30; N - 6.56; Found: C - 70.16; H - 7.33; Cl - 8.94; N - 6.53.

EXAMPLE 6

Acute Toxicity

Test animals were male mice (NMRI) weighing 18 to 23 g. The animals were fasted for 24 hours prior to the beginning of the test, water being available ad libitum. Each dose was tested in 6 animals, and was increased by a factor 1.5 to 2.0. The volume of liquid administered amounted to 2 ml in intragastric application and 1 ml/100 of body weight in subcutaneous application. The observation time was 48 hours.

EXAMPLE 7

Phenyl-p-quinone Test

Each dose was administered to 12 male mice weighing 18 to 23 g. Phenyl-p-quinone, 1.25 ml of a 0.02% solution per 100 g of body weight, was administered intraperitoneally 15 minutes after application of the substances to be investigated. Animals which did not show a typical pain reaction during the following 20 minutes were considered protected. The test was rejected is less than 10 out of 12 animals of the control group showed a reaction.

EXAMPLE 8

Photocage Test

Test animals were male white mice weighing 18 to 23 g. Spontaneous motility was measured in a glass cage (25 × 50 cm.) through the transverse of which three infrared rays pass equidistantly. The number of interruptions of the infrared rays within 30 minutes was considered to express spontaneous motility. Each test group comprised 5 animals. The substances were applied either intragastrically with a stomach tube or subcutaneously.

EXAMPLE 9

Temperature-reducing Effect

Test animals were male rats (SIV) weighing 80 to 120 g. The body temperature was determined within the framework of a behaviour test according to Irwin in which 5 rats were treated with the test substances after observation of normal behaviour and determination of the normal temperature. After 30, 60 and 120 minutes the rats were again subjected to the specific test program. The values shown in the chart represent the difference between the initial body temperature and the temperature taken 2 hours following administration of the substance. The body temperature was taken rectally with a thermometer made by the Ellab Company.

We claim:

1. A quaternary compound of the formula:

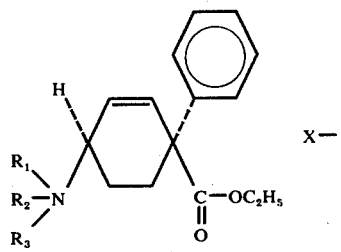

wherein $R_1$ and $R_2$ are the same or different and are hydrogen or alkyl of 1 to 4 carbons or one of the two groups is allyl, phenalkyl of 7 to 9 carbon atoms or α-methyl-β-hydroxyethyl, $R_3$ is alkyl of 1 to 4 carbon atoms and wherein X is a halide or acetate anion.

2. A compound according to claim 1 which is 4r-trimethylammonium-1t-phenyl-1c-ethoxycarbonyl-cyclohexene-(2) iodide.

3. A compound according to claim 1 which is 4r-trimethylammonium-1t-phenyl-1c-ethoxycarbonyl-cyclohexene-(2) acetate.

* * * * *